United States Patent [19]
Iles et al.

[11] Patent Number: 5,188,825
[45] Date of Patent: Feb. 23, 1993

[54] FREEZE-DRIED DOSAGE FORMS AND METHODS FOR PREPARING THE SAME

[76] Inventors: Martin C. Iles, 7 Cartwright Drive, Shaw, Swindon, Wiltshire; Angela D. Atherton, 170, Windsor Drive, Chelsfield, Orpington, Kent; Neil M. Copping, 8 Lautrec Way, Haydon Hill, Aylesbury, Bucks, all of United Kingdom

[21] Appl. No.: 458,311

[22] Filed: Dec. 28, 1989

[51] Int. Cl.$^5$ .............. A61K 31/74; A61K 9/68; A61K 9/14; A01N 25/08
[52] U.S. Cl. .............. 424/78.1; 424/78.08; 424/78.24; 424/78.31; 424/78.37; 424/439; 424/440; 424/441; 424/484; 424/486; 426/1; 426/2; 514/772.1; 514/772.2; 514/772.3; 514/772.4; 514/777; 514/778; 514/779; 514/780; 514/781; 514/782
[58] Field of Search .............. 424/439, 440, 441, 484, 424/486, 78.08, 78.1, 78.24, 78.31, 78.37; 426/1, 2; 514/772.1, 772.2, 772.4, 772.3, 777-782

[56] References Cited

U.S. PATENT DOCUMENTS

| | | | |
|---|---|---|---|
| 4,427,793 | 1/1984 | Reed et al. | 521/32 |
| 4,882,151 | 11/1989 | Yang et al. | 424/440 |

FOREIGN PATENT DOCUMENTS

| | | |
|---|---|---|
| 0122036 | 3/1984 | European Pat. Off. . |
| 0159237 | 3/1985 | European Pat. Off. . |
| 0308238 | 9/1988 | European Pat. Off. . |
| 1770882 | 7/1967 | Fed. Rep. of Germany . |
| 8804551 | 12/1986 | PCT Int'l Appl. . |
| 829245 | 10/1957 | United Kingdom . |
| 1548022 | 10/1976 | United Kingdom . |

*Primary Examiner*—Thurman K. Page
*Assistant Examiner*—Carlos Azpuru

[57] ABSTRACT

A method of preparing a freeze-dried dosage form including a water soluble active agent is disclosed. The water soluble active agent is bonded to an ion exchange resin to form a substantially water insoluble complex. This complex is then mixed with a compatible carrier and freeze-dried. The resulting freeze-dried dosage form contains an effective unit dosage amount of the active agent and exhibits enhanced compositional and physical stability, as well as permitting processing according to conventional freeze-drying techniques.

9 Claims, No Drawings

FREEZE-DRIED DOSAGE FORMS AND METHODS FOR PREPARING THE SAME

BACKGROUND OF THE INVENTION

1. Field of the Invention

The present invention relates to freeze-dried dosage forms and methods of preparing freeze-dried dosage forms.

2. Description of the Prior Art

Freeze-drying is a well known method of drying heat-sensitive materials in order to protect them from thermal damage. In the past, preparations containing active agents, such as pharmaceuticals, nutrients, diagnostics, fertilizers and insecticides, have been prepared by freeze-drying aqueous solutions or suspensions containing these active ingredients. Various freeze-dried dosage forms and methods for preparing such dosage forms are disclosed in United Kingdom Patent No. 1,548,022 and U.S. Pat. Nos. 4,490,407 and 4,642,903.

The inventors have determined that there are problems associated with the preparation of freeze-dried dosage forms containing water soluble active agents by means of the prior art techniques. Specifically, the inventors have found that the addition of water soluble active agents into a conventional freeze-dried carrier matrix reduces the physical stability of the resulting freeze-dried dosage form. The presence of water soluble active agents caused shrinkage, collapse and softening of the dosage form at increased rates and at lower relative humidities than for conventional freeze-dried dosage forms containing water insoluble active agents or for placebo freeze-dried dosage forms.

It is believed by the inventors that solutions or suspensions containing water soluble active agents may exhibit eutectic freezing characteristics. As the temperature of such a solution or suspension falls below 0° C., water will crystallize as ice, thereby causing an increase in the concentration of the active agent in the solution or suspension. As the temperature is lowered, ice crystallizes out until at a given temperature (the eutectic temperature), the concentration reaches the eutectic concentration and a eutectic solid forms. The eutectic solid is a mixture of ice crystals and the active agent. The eutectic temperature and concentration are independent of the initial concentration of the active agent in the solution or suspension. The volume of the eutectic solid, however, is dependent upon the initial concentration of the active agent. If the initial active agent concentration is high, then the active agent will crystallize out as the temperature of the solution or suspension falls, thereby reducing the active agent concentration of the solution or suspension until the eutectic solid forms at the eutectic temperature and concentration.

It is believed by the inventors that in order to achieve satisfactory freeze-drying of a solution or suspension containing a water soluble active agent, the solution or suspension must be frozen to or below the eutectic temperature and must remain below the eutectic temperature during drying. If the temperature is allowed to rise above the eutectic temperature, the eutectic solid melts. If the eutectic volume is small, this melting causes slow collapse of the resulting freeze-dried dosage form after drying. If the eutectic volume is large, the resulting freeze-dried dosage form exhibits excessive shrinkage and reduced physical stability. Since it is often impractical and expensive to carry out the freeze-drying process below the eutectic temperature, it has been difficult, if not impossible, to prepare satisfactory freeze-dried dosage forms containing water soluble active agents using conventional freeze-drying techniques.

The problems associated with freeze-drying water soluble active agents are not limited to active agents that form true eutectic compositions. Solutions or suspensions containing water soluble active agents may also exhibit the characteristics of glassy compositions. If the temperature of such a composition rises above the glass point, the glass flows or melts, resulting in the collapse or destruction of the freeze-dried dosage form.

The inventors have determined that the physical stability of a conventionally prepared freeze-dried dosage form containing a water soluble active agent may be enhanced by increasing the diameter of the freeze-dried dosage form. This in turn reduces the concentration of the active agent within the dosage form and alleviates the stability problems to some degree. However, this technique is quite limited in that the size of the dosage forms, especially those intended for oral administration, must not exceed a relatively small maximum size range. Furthermore, increasing the dosage size is not economical. The inventors have also determined that the presence of flavoring and sweetening agents renders conventional freeze-dried dosage forms containing water soluble active agents more stable. However, the presence of these additives does not completely alleviate the collapse, shrinkage and physical instability that results from using conventional freeze-drying techniques.

Another problem with trying to produce freeze-dried dosage forms incorporating a water soluble active agent is that the requisite freeze-drying times may be lengthened, thereby increasing the cost of producing the dosage forms. Although reducing the concentration of the active agent in the dosage form may minimize these adverse effects, this causes a corresponding increase in unit size in order to maintain the same effective unit dosage amount. This increase in size also contributes to an increase in processing costs. Thus, the use of conventional freeze-drying to produce dosage forms is practically limited to active agents that are water insoluble and there is a need for an improved freeze-dried dosage form for use with water soluble active agents.

Ion exchange resins are well known. These resins are capable of exchanging a cation or an anion for a variety of ions brought into contact with the resin. In the context of pharmaceutical active agents, it is known that ion exchange resins may be bonded to pharmaceuticals to form pharmaceutical/resin complexes having sustained release characteristics. See U.S. Pat. Nos. 2,990,332; 3,143,465; and 4,221,778; Borodkin et al., "Interaction of Amine Drugs with a Polycarboxylic Acid Ion-Exchange Resin," J. Pharm. Sci. 59(4): 481–486 (1970); Hinsvark et al., "The Oral Bioavailability And Pharmacokinetics Of Soluble And Resin-Bound Forms Of Amphetamine And Phentermine in Man," J. Pharmacokinetics And Biopharmaceutics 1(4): 319–328 (1973); Schlichting, "Ion Exchange Resin Salts For Oral Therapy I, Carbinoxamine," J. Pharm. Sci. 51(2): 134–136 (1962); Smith et al., "The Development Of A Liquid Antihistaminic Preparation With Sustained Release Properties," J. Amer. Pharm. Assoc. 49(2): 94–97 (1960); Hirscher et al., "Drug Release From . . . Cation Exchange Resins," J. Amer. Pharm. Assoc. NS2(2): 105–108 (1962); Amsel et al., "Dissolution And Blood Level Studies With a New Sustained Release System," R & SDC Proceedings 3:93–106 (1980); Amsel et al., "Unique Oral Controlled Release Systems: In Vivo Drug Release Pattern," (unpublished paper). In addition, it is known that ion exchange resins may be bound to pharmaceutical active agents in order to eliminate taste and odor problems in oral pharmaceutical dosage forms. See Borodkin et al., "Polycarboxylic Acid Ion-Exchange Resin Adsorbates for Taste Coverage in Chewable Tablets," J. Pharm. Sci. 60(10): 1523–1527 (1971); Specification Sheets for Amberlite IRP-64, Amberlite IRP-69 and Amberlite IRP-276, published by Rohm and Haas Company (1983).

SUMMARY OF THE INVENTION

It is an object of the present invention to provide a freeze-dried dosage form containing a water soluble active ingredient that is characterized by physical and compositional stability.

It is an additional object of the present invention to provide a method for preparing freeze-dried dosage forms containing a water soluble active ingredient having physical and compositional stability.

It is a further object of the present invention to provide a freeze-dried dosage form and methods for preparing the same that allow conventional freeze-drying processing conditions to be employed.

It is another object of the present invention to provide a freeze-dried dosage form and methods of preparing the same in economical unit sizes.

It is a specific object of the present invention to provide a freeze-dried dosage form containing an effective unit dosage amount of a water soluble active agent dispersed within a carrier that is compatible with the active agent. The active agent is bonded to or complexed with an ion exchange resin in order to form a substantially water insoluble active agent/resin complex. The active agent/resin complex is then dispersed within the carrier and freeze-dried to form a freeze-dried dosage form exhibiting improved physical and compositional stability.

It is another specific object of the present invention to provide a method of preparing a freeze-dried dosage form containing an effective unit dosage amount of a water soluble active agent. The inventive method comprises the step of freeze-drying a mixture containing: (a) a substantially water insoluble complex made from the active ingredient bonded to or complexed with an ion exchange resin, and (b) a carrier that is compatible with the active agent. The resulting freeze-dried dosage form exhibits improved compositional and physical stability.

Further objects and embodiments of the present invention will be made known in the following description of the preferred embodiments and claims. Although the following description of the preferred embodiment focuses on the inclusion of pharmaceuticals as the active agent, it is to be understood that the desirable properties of the inventive methods and dosage forms may be advantageously used in connection with many different types of active ingredients including, by way of example, nutrients, vitamins, minerals, diagnostics, fertilizers and insecticides.

DESCRIPTION OF THE PREFERRED EMBODIMENTS

The preferred freeze-dried dosage forms of the present invention contain three primary ingredients: (1) the water soluble active agent, (2) the carrier and (3) the ion exchange resin.

With respect to the active agent, a variety of active agents may be used in the present invention. Examples of such active agents are pharmaceuticals, nutritional agents, diagnostic agents and other chemical agents. Examples of pharmaceuticals that may be used with the present invention include phenylephrine hydrochloride, chlorpheniramine maleate, triprolidine hydrochloride, and pseudoephedrine hydrochloride. These drugs are all soluble in aqueous solutions and exhibit eutectic melting characteristics. Additionally, water soluble antipsychotic, antiulcer and antihistamine compounds may be used with the present invention. Another example of a pharmaceutical that may be used in the present invention is phenylpropanolamine hydrochloride, which forms a glass upon freezing. Other water soluble pharmaceuticals or drugs may likewise be used in the present invention. The pharmaceutical or drug should be present in the resulting freeze-dried dosage forms in an effective unit dosage amount for that particular drug or pharmaceutical.

Examples of nutritional agents that may be used with the present invention include vitamins, minerals and food supplements. Diagnostic agents, such as monoclonal antibodies, may be successfully incorporated into the present freeze-dried dosage forms. Other types of active chemical agents may also be used with the present invention, for example fertilizers and insecticides. Whatever active ingredient is incorporated into the inventive freeze-dried dosage form, it should be present in the resulting dosage form in an effective concentration per unit volume.

Any appropriate exchange resin may be used in the present invention as long as it is capable of reversibly binding to the particular desired active agent and is compatible with the active agent. In general, in order to bind a basic active agent ion, a cationic ion exchange resin should be used. Conversely, if an acidic active agent ion is to be used, an anionic ion exchange resin should be selected. Examples of the types of ion exchange resins that are useful are gel type resins and macroreticular type resins.

Gel type ion exchange resins are formed from the copolymerization of styrene and divinylbenzene. This gel matrix may be sulfonated to give a strongly acidic ion exchange resin. An example of such a resin is Amberlite Resin Grade IRP-69, a trade name of Rohm and Hass Company. In Amberlite IRP-69, the counter ion is sodium. This particular resin is approved for pharmaceutical use and is a cation exchange resin. An example of a gel type anionic exchange resin is Amberlite Resin Grade IRP-276, a trade name of Rohm and Haas Company. Amberlite IRP-276 is also a styrene divinylbenzene copolymer, but it contains quaternary ammonium anion exchange groups. The mobile or exchangeable anion in Amberlite IRP-276 is chloride. Amberlite IRP-276 is also approved for pharmaceutical use.

Macroreticular type resins that may be used in the present invention are formed from the copolymerization of methacrylic acid and divinylbenzene. The resulting porous matrix may be carboxylated to give a weakly acidic ion exchange resin. An example of such a resin is Amberlite Resin Grade IRP-64, a trade name of Rohm and Haas Company. In Amberlite IRP-64, the counter ion is a hydrogen ion. This resin is approved for pharmaceutical use.

In addition to gel type and macroreticular type resins, other types of ion exchange resins may be used in the present invention. Any ion exchange resin that is useful for sustained release or taste masking applications with pharmaceuticals may be used. An example of such a resin is Dowex 50, a sulfonic cation exchange resin and a trade name of Dow Chemical Company.

In order to prepare the active agent/ion exchange resin complexes that are used in the present invention, the following steps may preferably be followed. The ion exchange resin to be used may be washed by suspending the resin in purified water for 20 to 60 minutes with stirring. The resin may then be allowed to settle for 30 to 60 minutes. The supernatant may then be decanted, which will contain some fine particles of resin. The suspension and settling of the resin may be repeated two more times, stirring for 15 to 30 minutes and allowing the resin to settle out for 15 to 30 minutes.

The washed ion exchange resin may then be dried in an oven at approximately 60° C. for 18 hours. Alternatively, the washed resin may be dried by means of freeze-drying.

Preferably, before forming the active agent/resin complex, the washed and dried resin may be sieved through a 90 micron screen. If a screening step is used, the fraction of the resin that is less than 90 microns is used in forming the complex.

After washing, drying and sieving, the ion exchange resin may be suspended in an aqueous solution containing the active agent and stirred for one to twentyfour hours. The ratio of active agent concentration to ion exchange resin concentration is dependent upon the affinity of the active agent for the resin. Typically, the active agent:resin ratio may vary from between about 10:1 and about 1:5, with a range of between about 5:1 and about 1:5 being preferred. Most preferred is an active agent:ion exchange resin ratio of about 1:1 to about 1:3. All the above ratios are based on weight. The concentration of the active agent in the aqueous solution or suspension may vary from about 1 weight percent up to about 20 weight percent, with about 5 weight percent being a typical figure.

The resulting active agent/resin complex gives potencies of the active agent of approximately 5 percent up to about 50 percent. Maximum loading of the active agent on the ion exchange resin may be achieved with a high active agent to resin ratio. Maximum rate of take-up of the active agent onto the resin may be achieved with a low active agent concentration relative to the resin concentration.

To increase the rate of take-up of basic active agents onto Amberlite Resin IRP-64, the active agent solution may be adjusted to a pH of approximately 8.0. This reduces the concentration of hydrogen ions in solution, thereby facilitating the adsorption of active agent ions.

The resulting active agent/resin complex may be isolated by allowing it to settle out for approximately one hour. The supernatant may then be decanted from the precipitated complex. The complex may be washed twice with purified water by stirring for 10 to 30 minutes. The complex or resinate may be allowed to settle out for 10 to 30 minutes followed by decanting of the supernatant. The active agent/resin complex may then be dried in an oven at a temperature of up to 68° C. for up to approximately 24 hours. Alternatively, the active agent/resin complex may be dried by conventional freeze-drying techniques. The potency of the complex or resinate may than be assayed in order to determine the appropriate amount of complex or resinate to be incorporated into the freeze-dried dosage form so that the dosage form contains an effective unit dosage amount of the active agent.

The ion exchange resin/active agent complex is substantially insoluble in water. Therefore, it does not form a eutectic point or glass point system. Furthermore, the active agent remains bound to the ion exchange resin matrix while in aqueous suspension. The active agent, however, will be released in the presence of high concentration of competing counter ions. For example, complexes of an ion exchange resin and a pharmaceutical will disassociate in vivo, thereby releasing the soluble drug ion and leaving the insoluble, non-toxic, inert ion exchange matrix, which is typically not absorbed by the body.

In the context of the present invention, Amberlite Resin IRP-64 is advantageous as compared with Amberlite Resin IRP-69 in that IRP-64's in vitro active agent release rate is higher in 0.1N hydrochloric acid, as measured by a USP dissolution apparatus. However, the relevant literature indicates that the drug chlorpheniramine is released in vivo from a complex formed with Amberlite Resin IRP-69 and that this drug is then made 100% available for absorption by the body. Amberlite Resin IRP-64 is not effective with all active agents, since it has been found to be unsuitable for use with phenylephrine. Therefore, the appropriate ion exchange resin to be used in the present invention should be suitably selected with reference to the particular active agent desired to be incorporated into the resulting dosage form.

With respect to the carrier that may be used in the present invention, the most common element of the carrier will usually be water in order to form an aqueous solution or suspension. One or more bulk-forming agents may also be incorporated into the carrier solution or suspension prior to freeze-drying. The bulk-forming agent aids in maintaining the dispersion of the active agent/ion exchange resin within the carrier solution or suspension.

Any suitable, conventional bulk-forming agent may be used in connection with the present invention. Preferred bulk-forming agents include long chain polymers, for example, polypeptides such as gelatin or hydrolyzed gelatin, cellulose derivatives, alginate derivatives, polyvinylpyrrolidone, polyethylene glycols, polysaccharides, such as dextran, mannitol, sugars and starches and gums, such as acacia, xanthin, tragacanth and guar. The most preferred bulk-forming agents are gelatin, mannitol, xanthan gum and guar gum. The bulk-forming agents may be incorporated into the carrier solution or suspension in concentrations sufficient to aid in the maintenance of the dispersion of the active agent/resin complex within the solution or suspension.

The resulting carrier solution or suspension containing the active agent/resin complex may be freeze-dried by any conventional freeze-drying process. For example, the solution or suspension may be frozen by dispensing the solution or suspension into preformed molds and subsequently freezing such molds on refrigerated shelves or in refrigerated chambers. Alternatively, the molds containing the solution or suspension may be passed through a stream of cold gas or vapor, such as liquid nitrogen in a conventional freezing tunnel.

The frozen solution or suspension is then dried on heated shelves in a partially or completely evacuated chamber in accordance with conventional freeze-drying methods. In the case of frozen molded forms of the solution or suspension, these forms may be forced through an extrusion device such that the frozen solution or suspension is cut or formed into appropriately sized segments prior to drying.

In the case of a liquid nitrogen freezing tunnel, the freezing may occur at temperatures ranging from −40° C. down to −150° C. with residence times of the solution or suspension in the tunnel of between about 2 and about 20 minutes. Most preferably, the temperature in the freezing tunnel is maintained at about −70° C. down to about −80° C., with residence times of approximately 2.5 to 3 minutes. The condenser temperature during freeze-drying may be maintained in the range of about −40° C. to about −70° C., preferably between about −50° C. and about −60° C. The initial shelf temperature may range between about −40° C. up to about −10° C., with a range of about −20° C. to about −10° C. being preferred. The final shelf temperature may range between about +10° C. up to about +80° C., with the preferred range being between about +20° C. and +60° C. The chamber pressure may be maintained between about 0.05 mbar up to about 3 mbar, with the preferred range being between about 0.25 mbar and about 1.5 mbar. The cycle time may be as long as approximately 24 hours, with the preferred cycle time being between 1.5 hours up to about 4 hours.

Secondary components, such as flavorings, sweeteners, preservatives or colorings may also be incorporated into the freeze-dried dosage forms in accordance with conventional practices. For example, preservatives such as methylparabens, propylparabens, sodium methylhydroxybenzoate, sodium ethylhydroxybenzoate, and sodium butylhydroxybenzoate, may be included. Examples of sweetening agents that may be preferably used with the present invention includes aspartame, saccharin, sugar and Prosweet. Examples of flavoring agents that may be used with the present invention include menthol, aniseed, peppermint and tutti frutti. An example of a coloring agent that may be used in connection with the present invention is FD&C Yellow #5.

PRIOR ART EXAMPLE 1

Chlorpheniramine maleate is a water soluble antihistamine. Its solubility is approximately 1 part drug; 3.4 parts water at 20° C. and is usually given at a dose level of 1 to 4 mg. It has a eutectic melting point of approximately −20° C. Freeze-dried dosage forms were prepared from the following chlorpheniramine maleate solutions:

a) 2.67% (giving 4 mg in 150 mg solution)
b) 1.6% (giving 4 mg in 250 mg solution)
c) 0.8% (giving 4 mg in 500 mg solution).

Each solution also contained 4% gelatin USP and 3% mannitol BP to form the carrier or matrix. The solutions were dosed into blister packs, the pockets of which are the molds in which the units are formed. The solutions were frozen by passing through a liquid nitrogen food freezing tunnel and then freeze-dried. The resulting blister packs of dried units were then sealed and stored at a temperature of 30° C. and relative humidity of 75%.

Units not containing the drug/resin complex stored under the same conditions showed no visible change after 28 days of storage. The 0.15 g (wet dose weight) units at 28 days had shrunk to between 60% and 80% of their original diameter, the 0.25 g units to between 63% and 76% of their original diameter, and the 0.5 g units to between 87% and 97% of their original diameter. Disintegration times in water at 37° C. became extended within 3 days of storage for all three formulations.

EXAMPLE 2

A 2.6% solution of chlorpheniramine maleate in water was prepared. An ion exchange resin (Rohm and Haas Amberlite IRP-69) was added to give a ratio of 1 part drug to 3 parts resin. Monitoring of the concentration of drug in solution showed that 96% of the drug was absorbed onto the resin within one hour. The ion exchange resin was isolated from the solution by allowing the solid to sediment and decanting the supernatant. The supernatant was also filtered to obtain the smaller particle size material. The supernatant contains all ions not absorbed onto the ion exchange resin, including maleate ions. Thus the drug/resin complex presents the drug as the chlorpheniramine base and not as the maleate salt.

Freeze-dried dosage forms were prepared from a suspension formulated to give the equivalent dose of chlorpheniramine as 4 mg of the maleate salt per 0.15 g of suspension. The formulation contained 4% gelatin, 3% mannitol, 0.01% guar gum and 0.01% xanthan gum. The gums were added to reduce sedimentation of the ion exchange resin particles. The suspension was dosed, frozen and freeze-dried using similar conditions as in Example 1. The packs were sealed and stored at 30° C. and 75% humidity. At 28 days there was no visible change in appearance. Thus the stability of the 0.15 g (wet dose weight) freeze-dried dosage form containing chlorpheniramine equivalent to 4 mg of the maleate salt was greatly improved by use of the ion exchange resin/drug complex.

PRIOR ART EXAMPLE 3

Phenylephrine hydrochloride is a compound having a solubility of approximately 50% in water. It has a eutectic melting point of approximately −32° C. and is usually administered at a dose level of 10 mg. Freeze-dried dosage forms were prepared from the following phenylephrine HCl solutions:

a) 6.67% (10 mg per 150 mg solution)
b) 4% (10 mg per 250 mg solution)
c) 2% (10 mg per 500 mg solution)

Each solution also contained 4% gelatin USP and 3% mannitol BP. The formulations were dosed, frozen and freeze-dried using similar conditions to those used in Example 1.

The 6.67% solution could not be successfully freeze-dried due to its relatively low eutectic melting point unless a low shelf temperature was used, which led to extended drying cycle times (24 hours). On removal from the drier, the units prepared from 4% and 2% drug solutions were sticky, flexible and suffered from shrinkage at ambient temperature and humidity within 24 hours.

EXAMPLE 4

An ion exchange resin/drug complex of phenylephrine and Amberlite IRP-69 was prepared using the method of Example 2. Monitoring of the concentration of the drug in solution showed that 86% of the drug was absorbed onto the resin within one hour.

Freeze-dried dosage forms were prepared from a suspension formulated to give the equivalent dose of phenylephrine to 10 mg of phenylephrine hydrochloride per 0.25 g of suspension. The formulation also contained the same concentrations of gelatin, mannitol, guar gum and xanthan gum as in Example 2.

The sealed packs were placed on storage at 30° C. and 75% relative humidity, and were unchanged at 28 days.

COMPARATIVE EXAMPLES 5 AND 6

Freeze-dried dosage forms containing active agent-/Amberlite IRP-69 resin complex equivalent to 4 mg chlorpheniramine maleate in 150 mg (10 mm diameter units) for Example 5 and 10 mg phenylphrine hydrochloride in 250 mg (12 mm diameter units) for Example 6 were placed in unsealed packs at 20° C./75% relative humidity and in sealed packs at 30° C./75% relative humidity. The diameters and disintegration times of the dosage forms at 20° C. and 30° C. were measured at fixed time intervals.

The drug:resin complexes were prepared with a drug:resin ratio of 1:3. The complexes were isolated, washed and freeze-dried before incorporation into the following formulations:

Chlorpheniramine (Example 5)

To give a 4 mg chlorpheniramine maleate dose, the amount of 1:3 drug:resin complex required was 24.8232 mg per 10 mm dosage form. The formulation also included flavoring and thickening or bulk-forming agents as follows:
4% gelatin
3% mannitol
0.75% cherry (Virginia Dare Extract Co. #761)
0.1% aspartame
0.1% menthol
9.88% chlorpheniramine/IRP-69 complex
0.01% xanthan gum
0.01% guar gum
water to 100%.

Phenylephrine (Example 6)

To give a 10 mg phenylephrine hydrochloride dose, the amount of 1:3 drug:resin complex required was 38.257 mg per 12 mm dosage form. The final formulation contained 15.3% of the phenylephrine/IRP-69 complex with the remaining excipients as in Example 5.

Prepared suspensions were dosed into 200 micron PVC/40 gsm PVdC packs using a Gilson pipeteman (chlorpheniramine in a 0.150 g dose in 10 mm units; phenylephrine in a 0.25 g dose in 12 mm units). Dosed packs were frozen in a liquid nitrogen freeze tunnel at −70° C. with a 3 minute residence time, and the frozen units were dried at a shelf temperature of 30° C. and a chamber pressure of 1 mbar. The packs were sealed with 40 micron soft temperature foil using a Sharp Interpack sealing machine.

Units from each sample were examined for appearance, diameter and their disintegration times in water at 20° C. and 37° C. Packs were also stored unsealed at 20° C./75% relative humidity and sealed at 30° C./75% relative humidity and examined at set time intervals.

Both formulations produced evenly colored beige units but the upper surfaces of some of the chlorpheniramine units were crystalline and mottled. All units had slight frost heave and fell out of the blister pockets if the packs were inverted. The unit diameters and disintegration times at 20° C. and 37° C. throughout the stability storage time are shown in Tables 1-4 below. Initially both the chlorepheniramine and phenylephrine units wetted quickly with subsequent dispersion, the wetting and dispersion being slower at 20° C. The chlorpheniramine units dispersed faster than the phenylephrine units, probably due to the lower solids content.

Units stored unsealed at 20° C./75% relative humidity showed a trend of decreasing diameter (most marked after week 1), and longer wetting times with a concomitant decrease in unit dispersion (see Tables 1 and 3). After 12 weeks the chlorpheniramine units were badly shrunken and exhibited long wetting times with no dispersion. Insufficient units were available for 12 weeks data on phenylephrine but at 8 weeks the units were badly shrunken and showed no wetting at 20° C.

TABLE 1

| | 10 mm Chlorpheniramine units, stored unsealed at 20° C./75% RH | | |
|---|---|---|---|
| Time on Stability (weeks) | Unit Diameter (mm) | Disintegration time (20° C.) (sec) | Disintegration time (37° C.) (sec) |
| 0 | 9.37 ± 0.04 | 3-4 sec to wet and break up, fair dispersion. | 1-2 sec to wet and break up quite good dispersion. |
| 1 | 8.70 ± 0.06 | 6.9 ± 0.7 No dispersion. | >10 sec to wet, no dispersion. |
| 2 | 8.65 ± 0.10 | 6.2 ± 0.2 No dispersion | 4-5 sec No dispersion |
| 3 | 8.51 ± 0.22 | 10.1 ± 2.1 No dispersion. | Wets initially then forms a plug. |
| 4 | 8.49 ± 0.15 | 3.0 ± 0.4 No dispersion | 1.5 ± 0.2 Slight dispersion. |
| 8 | 7.98 ± 0.13 | Wetting at edges, remainder of unit very slow, no dispersion. | Wetting at edges, remainder of unit very slow. No dispersion. |
| 12 | 8.01 ± 0.14 | Not measured | Full wetting >60 sec, no dispersion. |

TABLE 2

| | 10 mm Chlorpheniramine units, stored sealed at 30° C./75% RH | | |
|---|---|---|---|
| Time on Stability (weeks) | Unit Diameter (mm) | Disintegration time (20° C.) (sec) | Disintegration time (37° C.) (sec) |
| 0 | 9.37 ± 0.04 | 3-4 sec to wet | 1-2 sec to wet and break up |

TABLE 2-continued 10 mm Chlorpheniramine units, stored sealed at 30° C./75% RH

| Time on Stability (weeks) | Unit Diameter (mm) | Disintegration time (20° C.) (sec) | Disintegration time (37° C.) (sec) |
|---|---|---|---|
|  |  | and break up, fair dispersion. | quite good dispersion. |
| 1 | 9.49 ± 0.07 | 3.7 ± 0.4 No dispersion. | 1.7 ± 0.4 Good dispersion. |
| 2 | 9.24 ± 0.07 | 2.3 ± 0.2 No dispersion | 1-1.5 Wet and break up. |
| 3 | 9.41 ± 0.08 | 3.6 ± 1.1 Fair disp. around edges. | 3.3 ± 1.2 Fair dispersion. |
| 4 | 9.43 ± 0.08 | 2.1 ± 0.1 Dispersion only around edges. | 1.0 ± 0.3 Complete dispersion. |
| 8 | 9.23 ± 0.03 | 2.0 ± 0.7 Dispersion from edges only. | 1.3 ± 0.3 Very good dispersion. |
| 12 | 9.03 ± 0.14 | Most of unit wet at 15-20 sec small areas taking >60 sec Wetted areas disperse. | Full wetting ~50 sec Dispersion from edges. |

TABLE 3

12 mm phenylephrine units, stored unsealed at 20° C./75% RH

| Time on Stability (weeks) | Unit Diameter (mm) | Disintegration time (20° C.) (sec) | Disintegration time (37° C.) (sec) |
|---|---|---|---|
| 0 | 11.05 ± 0.04 | 2-3 sec to wet and break up, dispersion very poor | 2-2.5 sec to wet and break up, fair dispersion. |
| 1 | 10.31 ± 0.04 | >10 sec to wet, no dispersion. | 6-8 sec to wet, no dispersion. |
| 2 | 10.10 ± 0.04 | 10 sec to wet, no dispersion | 3-4 sec No dispersion |
| 3 | 10.03 ± 0.06 | 13.3 ± 1.7 very poor dispersion. | 8.6 ± 4.2 Poor dispersion. |
| 4 | 9.93 ± 0.15 | Very slow wetting, no dispersion | 3.3 ± 0.8 Poor wetting, no dispersion. |
| 8 | 9.36 ± 0.06 | No wetting | 1.20 ± 0.2 No dispersion. |
| 12 | — | NOT TESTED (insufficient units) | — |

TABLE 4

12 mm phenylephrine units, stored sealed at 30° C./75% RH

| Time on Stability (weeks) | Unit Diameter (mm) | Disintegration time (20° C.) (sec) | Disintegration time (37° C.) (sec) |
|---|---|---|---|
| 0 | 11.05 ± 0.04 | 2-3 sec to wet and break up, dispersion very poor | 2-2.5 sec to wet and break up, fair dispersion. |
| 1 | 11.12 ± 0.03 | 2.4 ± 0.3, partial dispersion. | 1.8 ± 0.4 Fair dispersion. |
| 2 | 11.07 ± 0.06 | 4.7 ± 0.4 No dispersion | 2-3 sec No dispersion |
| 3 | 11.20 ± 0 | 8.9 ± 1.4 Dispersion around edges only. | 5.0 ± 1.9 Fair dispersion. |
| 4 | 11.13 ± 0.04 | 5.6 ± 2.0 No dispersion. | 1.2 ± 0.1 No dispersion. |
| 8 | 10.99 ± 0.06 | Patchy wetting, dispersion from edges only. | Patchy wetting, fair dispersion. |
| 12 | 10.84 ± 0.02 | Not measured. | Most of unit wet in 10 sec small areas remain dry upto 60 sec. Little dispersion. |

In contrast, units stored sealed at 30° C./75% relative humidity did not show a significant decrease in diameter until 12 weeks storage. Unit wetting times became slightly longer (more noticeable for phenylephrine units) but unit dispersion was variable. After 12 weeks wetting was still occurring but with little dispersion.

The data for chlorpheniramine/resin complex units compares very favorably with data reported previously for 4 mg chlorpheniramine maleate units. The 10 mm chlorpheniramine maleate units were shown to shrink rapidly when stored sealed at 30° C./75% relative humidity. The units were spongy after 5 days and totally shrivelled after 28 days. Increasing the unit size was, however, shown to increase the physical stability of the units.

Stability data for 16 mm 4% gelatin, 3% mannitol placebo units stored sealed at 30° C./75% relative humidity showed that the units started to shrink badly after 8 weeks. After 12 weeks the units had shrunk from 14.89 mm to 12.65 mm and were only slowly wetting with no dispersion at 20° C. The data for both the chlorpheniramine and the phenylephrine units compares very well with this data.

Ten millimeter units containing a chlorpheniramine/IRP-69 resin complex equivalent to 4 mg chlorpheniramine maleate had greatly improved stability when stored sealed at 30° C./75% relative humidity, when compared to 10 mm units containing 4 mg chlorpheniramine maleate. For 12 mm phenylephrine units (equivalent to 10 mg phenylephrine hydrochloride) the resin complex produced units that were much more stable than the units prepared from noncomplexed drug. Stability also compared favorably with 16 mm placebo units. The use of drug/resin complexes effectively removes the drug from solution and appears to lead to the production of stable units.

COMPARATIVE EXAMPLE 7

Washed, dried drug resinate powder was formulated into a freeze-dried dosage form. The resinate was added at a concentration to give the correct amount of drug base equivalent to the dose level of the normally used salt. For example for chlorpheniramine maleate, a normal dose level of 4 mg of salt is equivalent to 2.813 mg of base, which in turn is equivalent to 11.87 mg of a 23.7% potent resinate.

Freeze-dried dosage forms containing 4 mg chlorpheniramine maleate were prepared using normal processing conditions. The drug powder was suspended to give 4 mg of drug per 150 mg of formulation (10 mm diameter unit). The data showed however that on storage at 30° C./75% relative humidity, noticeable deterioration of these units occurred within 11 days. At lower drug concentrations, 4 mg per 250 mg (12 mm) and 4 mg per 500 mg (16 mm), the physical stability was improved but deterioration had commenced before 28 days, even at the lowest drug concentration studied. This compares with little change seen at 8 weeks in a similar placebo unit.

In comparison, 10 mm diameter unit containing chlorpheniramine/IRP-69 resinate at a concentration equivalent to 4 mg of the maleate salt showed little change at up to 4 weeks with the units being visually acceptable at 12 weeks.

COMPARATIVE EXAMPLE 8

Freeze-dried dosage forms containing 10 mg of phenylephrine hydrochloride were prepared at drug concentrations of 10 mg per 150 mg (10 mm diameter units), 10 mg per 250 mg (12 mm) and 10 mg per 500 mg (16 mm). Colder than normal freezing conditions were required to freeze the solutions.

During freeze-drying under standard drying conditions the 10 mm units (highest drug concentration) collapsed, i.e., the structure was destroyed. The 12 mm and 16 mm units were sticky and flexible and also began to collapse within 24 hours of storage at ambient temperatures and relative humidity. The 10 mg drug per 150 mg formulation was freeze-dried successfully but only over a period of 24 hours.

In comparison, a 12 mm diameter unit containing phenylphrine/IRP-69 resinate at a concentration equivalent to 10 mg of the hydrochloride salt was prepared successfully using normal processing conditions. The resulting units were placed on storage at 30° C./75% relative humidity showed little physical deterioration after 4 weeks, and the units were visually acceptable after 12 weeks of storage.

EXAMPLE 9

An allergy product containing chlorpheniramine was formulated using a chlorpheniramine/IRP-64 complex with a drug:resin ratio of 1:2. 250 mg of the formulation below was filled into a pocket diameter of 12 mm and freeze-dried.

Gelatin: 7.5 mg
Mannitol: 7.5 mg
Xanthan Gum: 0.062 mg
Guar Gum: 0.062 mg
Methyl Parabens: 0.1875 mg
Propyl Parabens: 0.0625 mg
Aspartame: 1.0 mg
Peppermint flavor: 0.50 mg
Chlorpheniramine/IRP-64: 11.87 mg
Purified Water: 221.255 mg.

EXAMPLE 10

A cough/cold dosage form including chlorphenarimine/IRP-69 (1:1) and phenylephrine/IRP-69 (1:2) was prepared. The formulation given below was filled into a pocket diameter of 16 mm in the amount of 500 mg and freeze-dried.

Gelatin: 15 mg
Mannitol: 15 mg
Xanthan Gum: 0.25 mg
Guar Gum: 0.25 mg
Methyl Parabens: 0.375 mg
Propyl Parabens: 0.125 mg
Aspartame: 2 mg
Peppermint flavor: 1 mg
Chlorpheniramine/IRP-69: 7.34 mg
Phenylephrine/IRP-69: 32.9 mg
Purified Water: to 500 mg.

EXAMPLE 11

A cough/cold dosage form was prepared according to the process described in Example 10 using the following formulation.

Gelatin: 15 mg
Mannitol: 15 mg
Xanthan Gum: 0.125 mg
Guar Gum: 0.125 mg
Methyl Parabens: 0.375 mg
Propyl Parabens: 0.125 mg
Aspartame: 2 mg
Peppermint flavor: 1 mg
Chlorpheniramine/IRP-69: 7.34 mg
Phenylephrine/IRP-69: 32.90 mg
FD&C Yellow No. 5 A1 Lake: 0.25 mg
Purified Water: 425.76 mg.

EXAMPLE 12

250 grams of chlorpheniramine maleate were dissolved in 4750 g of purified water to give a 5% w/w solution. This solution was adjusted to a pH of 8.0 by the addition of 10M sodium hydroxide solution. 500 grams of washed, dried Amberlite resin IRP-69 was suspended in this solution and the suspension was stirred for 60 minutes. The drug/resinate particles were allowed to settle for 25 minutes and then the supernatant was decanted. The drug resinate was resuspended in purified water for 10 minutes and then allowed to settle for 15 minutes. The supernatant washings were decanted, and the washing procedure repeated a second time. Approximately 90% of the drug was adsorbed into the resin. The potency of the resinate was assayed at 0.237 g chlorpheniramine base to 1 g of resinate (23.7%).

EXAMPLE 13

An ion exchange resin/drug complex of an antipsychotic compound and Amberlite IRP-64 resin was prepared using the method of Example 2. The potency of the resulting complex was 23%. Freeze dried dosage forms were prepared from a suspension formulated to give 10 mg of the active agent per 0.150 g of suspension. When compared with units prepared from active agent alone the ion exchange units showed much better appearance, handling and stability characteristics, indicating a more successful drying of the frozen product.

The use of an ion exchange resin/active agent complex makes possible the production of freeze-dried dosage forms containing water soluble active agents by improving physical stability and reducing freeze-drying cycle times, thereby reducing costs. For example, an aqueous solution of phenylephrine hydrochloride has a eutectic melting point of $-32°$ C. Freeze-dried dosage forms containing this drug at concentrations of 1% or greater cannot successfully be manufactured by conventional techniques. By contrast, a complex of phenylephrine and an ion exchange resin, such as Amberlite IRP-69, when suspended in an aqueous phase does not reduce the melting point of the phase, enabling it to be freeze-dried successfully even at concentrations of the complex equivalent to 6.6% of the hydrochloride salt.

The inventive freeze-dried dosage forms are also useful in that they reduce the undesirable odor and/or taste of active agents. For example, both chlorpheniramine maleate and phenylephrine hydrochloride have strong, quite unpleasant tastes. The ion exchange resin complexes formed with these two drugs, however, are tasteless. Further, the freeze-dried dosage forms resulting from the present invention often are capable of rapid disintegration, i.e., disintegration in less than 10 seconds in water. It is to be understood that the preceding description of the preferred embodiments has emphasized certain embodiments by way of example. Numerous other embodiments not specifically discussed may nevertheless fall within the spirit and scope of the present invention or the following claims.

We hereby claim as our invention:

1. A method of preparing a freeze-dried solid dosage form for oral administration containing an effective unit dosage amount of a water soluble bioactive agent comprising the following step: freeze-drying an aqueous suspension consisting essentially of a) a substantially water insoluble bound bioactive agent complex consisting essentially of the bioactive agent bound to an ion exchange resin and b) an aqueous carrier compatible with the bioactive agent consisting essentially of water and a bulk-forming agent selected from the group consisting of gelatin, polyvinylpyrrolidone, polyethylene glycol, polysaccharides, and combinations thereof.

2. The method of claim 1 wherein the bioactive agent is a pharmaceutical.

3. The method of claim 2 wherein the bioactive agent is selected from the group consisting of phenylephrine hydrochloride, chlorpheniramine maleate, triprolidine hydrochloride, pseudoephedrine hydrochloride and phenylpropanolamine hydrochloride.

4. The method of claim 1 wherein the ion exchange resin is a cationic ion exchange resin.

5. The method of claim 1 wherein the ion exchange resin is an anionic ion exchange resin.

6. The method of claim 1 wherein the ion exchange resin is a gel resin.

7. The method of claim 1 wherein the ion exchange resin is a macroreticular resin.

8. The method of claim 1 wherein the gelatin comprises hydrolyzed gelatin.

9. The method of claim 1 wherein the polysaccharides are selected from the group consisting of hydrolyzed gelatin, cellulose derivatives, alginate derivatives, dextran, mannitol, sugar, starches, gums, acacia, xanthan gum, guar gum, and combinations thereof.

* * * * *